United States Patent
Korytko et al.

(10) Patent No.: US 10,913,799 B2
(45) Date of Patent: Feb. 9, 2021

(54) ANTI-RANKL ANTIBODIES AND USES THEREOF

(71) Applicant: Eli Lilly and Company, Indianapolis, IN (US)

(72) Inventors: Andrew Ihor Korytko, Oceanside, CA (US); Victor H Obungu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 136 days.

(21) Appl. No.: 16/340,290

(22) PCT Filed: Oct. 20, 2017

(86) PCT No.: PCT/US2017/057543
§ 371 (c)(1),
(2) Date: Apr. 8, 2019

(87) PCT Pub. No.: WO2018/080914
PCT Pub. Date: May 3, 2018

(65) Prior Publication Data
US 2019/0284289 A1    Sep. 19, 2019

Related U.S. Application Data

(60) Provisional application No. 62/414,217, filed on Oct. 28, 2016.

(51) Int. Cl.
| | | |
|---|---|---|
| *C07K 16/24* | (2006.01) | |
| *C07K 16/28* | (2006.01) | |
| *A61P 19/10* | (2006.01) | |
| *A61K 39/00* | (2006.01) | |

(52) U.S. Cl.
CPC ......... *C07K 16/2875* (2013.01); *A61P 19/10* (2018.01); *A61K 2039/505* (2013.01); *C07K 2317/34* (2013.01); *C07K 2317/76* (2013.01); *C07K 2317/92* (2013.01)

(58) Field of Classification Search
CPC ............................ C07K 16/2875; A61P 19/10
See application file for complete search history.

(56) References Cited

U.S. PATENT DOCUMENTS

| | | | |
|---|---|---|---|
| 6,740,522 B2 | 5/2004 | Anderson | |
| 7,364,726 B2* | 4/2008 | Hiserodt | A61K 35/13 424/93.2 |
| 2018/0118840 A1* | 5/2018 | Obungu | C07K 16/2875 |

FOREIGN PATENT DOCUMENTS

| | | | | |
|---|---|---|---|---|
| EP | 3085709 A1 | 10/2016 | | |
| WO | 2007/059136 A2 | 5/2007 | | |
| WO | 2014/159430 A1 | 10/2014 | | |
| WO | 2015/030701 A1 | 3/2015 | | |
| WO | 2016/186957 A1 | 11/2016 | | |
| WO | WO-2016186957 A1 * | 11/2016 | ....... | A61K 39/39591 |
| WO | WO-2017136195 A1 * | 8/2017 | ............. | A61P 19/10 |

OTHER PUBLICATIONS

Furuya, et al. "Increased Bone Mass in Mice after single injection of Anti-receptor Activator of Nuclear Factor-B Ligand-neutralizing Antibody: Evidence for bone anabolic effect of parathyroid hormone in mice with few osteoclasts", Journal of Biological Chemistry, vol. 286, No. 42, Oct. 21, 2011.

Sri Harsha Tella, et al. "Biological agents in management of osteoporosis", European Journal of Clinical Pharmacy., vol. 71, No. 11, Nov. 11, 2014, 1291-1301.

\* cited by examiner

*Primary Examiner* — Claire Kaufman
(74) *Attorney, Agent, or Firm* — Duane Marks

(57) ABSTRACT

Antibodies and methods of using these antibodies are provided which bind human and mouse receptor activator of nuclear factor kappa-B ligand, said antibodies are useful as agents for treating conditions associated with bone-related disorders or skeletal abnormalities caused by cancer.

10 Claims, No Drawings

Specification includes a Sequence Listing.

ANTI-RANKL ANTIBODIES AND USES THEREOF

The present invention is in the field of medicine. More particularly, the present invention relates to antibodies and pharmaceutical compositions thereof, that include an antibody directed against receptor activator of nuclear factor kappa-B ligand (RANKL). The antibodies of the present invention are expected to be useful in the treatment of bone-related disorders such as osteoporosis, osteopenia, and arthritis (such as rheumatoid arthritis), and skeletal abnormalities caused by cancers such as non-small cell lung cancer and multiple myeloma.

Bone-related disorders affect millions of individuals, often causing painful and debilitating symptoms. Osteoporosis, a common metabolic bone-related disorder, is characterized by progressive loss of bone mass resulting, at least in part, from excessive osteoclastic bone resorption relative to osteoblastic bone formation. The loss of bone mass associated with osteoporosis puts bones at a greater risk of fracture. Long-term consequences of osteoporosis-associated loss of bone mass can result in severe physical consequences including bone fractures, chronic pain, disability, and/or immobility, as well as rendering the skeleton unable to provide adequate structural support for the body.

RANKL is a member of the TNF-superfamily of proteins and plays an important role in bone remodeling. RANKL is expressed by osteoblasts and binds its cognate receptor RANK on the surface of osteoclasts and osteoclast precursor cells. Binding of RANKL to RANK induces the formation, activation, and survival of mature osteoclasts and the stimulation of intracellular signaling cascades leading to increased bone resorption. Neutralizing antibodies to RANKL are known in the art. For example, U.S. Pat. No. 6,740,522 discloses anti-RANKL antibodies including Denosumab, marketed under the names Prolia® and Xgeva®, which is the only approved anti-RANKL therapeutic antibody (approved for the treatment of osteoporosis in postmenopausal women and men at high risk for fracture and prevention of skeletal-related events in patients with bone metastases from solid tumors, respectively).

Osteoporosis-related fractures constitute a major health concern and economic burden for health care systems. According to the National Osteoporosis Foundation, 9.9 million Americans have osteoporosis and an additional 43.1 million suffer from low bone density. Annually, over two million bone fractures and more than four-hundred thousand hospital admissions are attributed to osteoporosis. The U.S. Surgeon General estimates osteoporosis-related bone fractures result in direct care expenditure of between twelve and eighteen billion dollars annually.

Current therapies are not amenable to co-administration or co-formulation with other agents, such as anti-resorptive or anabolic compounds. Moreover, there is a lack of anti-RANKL antibodies that are useful to study in in vivo pre-clinical models such as murine models. Thus, there remains a need for alternative therapies for bone-related disorders or skeletal abnormalities caused by cancer, which could lead to better outcomes for patients. Such alternative therapy will preferably be capable of demonstrating efficacy in treatment of bone-related disorders such as osteoporosis, osteopenia, and arthritis (such as rheumatoid arthritis), and in treatment of skeletal abnormalities caused by cancers such as non-small cell lung cancer and multiple myeloma. The antibodies of the present invention provide an alternative therapy that is expected to meet at least one of the above needs.

The present invention provides antibodies that bind RANKL, wherein the antibodies comprise a light chain variable region (LCVR) and a heavy chain variable region (HCVR), wherein the LCVR comprises complementarity determining regions (CDRs) LCDR1, LCDR2, and LCDR3, and the HCVR comprises CDRs HCDR1, HCDR2, and HCDR3, wherein the amino acid sequence of LCDR1 is SEQ ID NO: 12, the amino acid sequence of LCDR2 is SEQ ID NO: 13, the amino acid sequence of LCDR3 is SEQ ID NO: 14, the amino acid sequence of HCDR1 is SEQ ID NO: 9, the amino acid sequence of HCDR2 is SEQ ID NO: 10, and the amino acid sequence of HCDR3 is SEQ ID NO: 11. In some particular embodiments, Xaa at position 6 of the amino acid sequence given by SEQ ID NO: 11 is Ala; Xaa at position 14 of the amino acid sequence given by SEQ ID NO: 11 is Pro; and Xaa at position 4 of the amino acid sequence given by SEQ ID NO: 14 is Trp. In other particular embodiments, Xaa at position 6 of the amino acid sequence given by SEQ ID NO: 11 is Arg; Xaa at position 14 of the amino acid sequence given by SEQ ID NO: 11 is Tyr; and Xaa at position 4 of the amino acid sequence given by SEQ ID NO: 14 is Asn.

In some particular embodiments, the present invention provides antibodies in which the LCVR has an amino acid sequence given by SEQ ID NO: 4 or SEQ ID NO: 8, and the HCVR has an amino acid sequence given by SEQ ID NO: 3 or SEQ ID NO: 7. In some particular embodiments, the LCVR has an amino acid sequence given by SEQ ID NO: 4, and the HCVR has an amino acid sequence given by SEQ ID NO: 3. In other particular embodiments, the LCVR has an amino acid sequence given by SEQ ID NO: 8, and the HCVR has an amino acid sequence given by SEQ ID NO: 7.

In some particular embodiments, the present invention provides antibodies in which the LC has an amino acid sequence given by SEQ ID NO: 2 or SEQ ID NO: 6. In further embodiments, the present invention provides antibodies in which the HC has an amino acid sequence given by SEQ ID NO: 1 or SEQ ID NO: 5. In some such embodiments, the LC has an amino acid sequence given by SEQ ID NO: 2, and the HC has an amino acid sequence given by SEQ ID NO: 1. In other such embodiments, the LC has an amino acid sequence given by SEQ ID NO: 6, and the HC has an amino acid sequence given by SEQ ID NO: 5.

In some embodiments, the antibodies of the present invention bind human RANKL. In other such embodiments, the antibodies of the present invention bind murine RANKL. In other such embodiments, the antibodies of the present invention bind human RANKL and murine RANKL.

The present invention also relates to nucleic acid molecules and expression vectors encoding the antibodies of the present invention. In an embodiment, the present invention provides a DNA molecule comprising a polynucleotide sequence encoding the HC, wherein the amino acid sequence of the HC is SEQ ID NO: 1. According to some such embodiments, the DNA molecule has a polynucleotide sequence given by the SEQ ID NO: 15.

In an embodiment, the present invention also provides a DNA molecule comprising a polynucleotide sequence encoding the LC, wherein the amino acid sequence of the LC is SEQ ID NO: 2. According to some such embodiments, the DNA molecule has a polynucleotide sequence given by the SEQ ID NO: 16.

In a further embodiment, the present invention provides a DNA molecule comprising a polynucleotide sequence encoding the HC having the amino acid sequence of SEQ ID NO: 1, and comprising a polynucleotide sequence encoding the LC having the amino acid sequence of SEQ ID NO: 2. In a particular embodiment the polynucleotide sequence encoding the HC having the amino acid sequence of SEQ ID NO: 1 is given by SEQ ID NO: 15, and the polynucleotide sequence encoding the LC having the amino acid sequence of SEQ ID NO: 2 is given by SEQ ID NO: 16.

The present invention also provides a mammalian cell transformed with DNA molecule(s), which cell is capable of expressing an antibody comprising the HC and the LC of the present invention, wherein the HC has an amino acid sequence given by SEQ ID NO: 1 and the LC has an amino acid sequence given by SEQ ID NO: 2. Also, the present invention provides a process for producing an antibody comprising the HC and the LC, comprising cultivating the mammalian cell under conditions such that the antibody of the present invention is expressed. The present invention also provides an antibody produced by said process. The present invention also provides a mammalian cell transformed with DNA molecule(s), which cell is capable of expressing an antibody comprising two HC and two LC of the present invention, wherein each HC has an amino acid sequence given by SEQ ID NO: 1 and each LC has an amino acid sequence given by SEQ ID NO: 2. Also, the present invention provides a process for producing an antibody comprising two HC and two LC, comprising cultivating the mammalian cell under conditions such that the antibody of the present invention is expressed. The present invention also provides an antibody produced by said process.

The present invention also provides a pharmaceutical composition comprising an antibody of the present invention and one or more pharmaceutically acceptable carriers, diluents, or excipients. Pharmaceutical compositions of the present invention can be used in the treatment of a bone-related disorder, whereby such treatment comprises administering to a patient in need thereof a therapeutically effective amount of a pharmaceutical composition of the present invention. In some such embodiments, the bone-related disorder is one or more of osteoporosis, osteopenia, and arthritis (such as rheumatoid arthritis). In other such embodiments, pharmaceutical compositions of the present invention can be used in the treatment of skeletal abnormalities caused by cancer, whereby such treatment comprises administering to a patient in need thereof a therapeutically effective amount of a pharmaceutical composition of the present invention. In particular embodiments, the cancer is one or more of non-small cell lung cancer and multiple myeloma.

The present invention also provides a method of treating a bone-related disorder or skeletal abnormalities caused by cancer comprising administering to a patient in need thereof a therapeutically effective amount of an antibody of the present invention. In some such embodiments, the bone-related disorder is osteoporosis. In some such embodiments, the bone-related disorder is osteopenia. In some such embodiments, the bone-related disorder is arthritis. In a more particular embodiment, the bone-related disorder is rheumatoid arthritis. In other such embodiments, the bone-related disorder is one or more of osteoporosis, osteopenia, and arthritis (such as rheumatoid arthritis). The present invention also provides a method of treating one or more of skeletal abnormalities caused by non-small cell lung cancer and skeletal abnormalities caused by multiple myeloma.

The present invention also provides an antibody of the present invention or pharmaceutical composition thereof for use in therapy. More particularly, the present invention provides an antibody of the present invention or pharmaceutical composition thereof for use in the treatment of one or more of osteoporosis, osteopenia, and arthritis (such as rheumatoid arthritis). The present invention also provides an antibody of the present invention or pharmaceutical composition thereof for use in the treatment of one or more of skeletal abnormalities caused by non-small cell lung cancer and skeletal abnormalities caused by multiple myeloma.

The present invention also provides the use of an antibody of the present invention or pharmaceutical composition thereof in the manufacture of a medicament for the treatment of a bone-related disorder or skeletal abnormalities caused by cancer. According to some particular embodiments, the present invention provides antibodies of the present invention or pharmaceutical compositions thereof in the manufacture of a medicament for the treatment of at least one or more of osteoporosis, osteopenia, and arthritis (such as rheumatoid arthritis). The present invention also provides an antibody of the present invention or pharmaceutical composition thereof in the manufacture of a medicament for the treatment of one or more of skeletal abnormalities caused by non-small cell lung cancer and skeletal abnormalities caused by multiple myeloma.

In an embodiment, the antibodies of the present invention bind human RANKL at one or more of residues 89-97, and one or more of residues 125-132, of SEQ ID NO: 17. In another embodiment, the antibodies of the present invention bind an epitope on human RANKL, wherein the epitope comprises at least one amino acid of residues 89-97, and at least one amino acid of residues 125-132, of SEQ ID NO: 17. In a further embodiment, the epitope comprises at least two amino acids of residues 89-97, and at least two amino acids of residues 125-132, of SEQ ID NO: 17. In another further embodiment, the epitope comprises at least three amino acids of residues 89-97, and at least three amino acids of residues 125-132, of SEQ ID NO: 17. In another further embodiment, the epitope comprises at least four amino acids of residues 89-97, and at least four amino acids within 125-132, of SEQ ID NO: 17. In another further embodiment, the epitope comprises at least five amino acids of residues 89-97, and at least five amino acids of residues 125-132, of SEQ ID NO: 17.

In an embodiment, the present invention provides an antibody that is capable of competing for binding human RANKL with an antibody comprising LCDR1, LCDR2, LCDR3, HCDR1, HCDR2, and HCDR3, wherein the amino acid sequence of LCDR1 is SEQ ID NO: 12, the amino acid sequence of LCDR2 is SEQ ID NO: 13, the amino acid sequence of LCDR3 is SEQ ID NO: 14, the amino acid sequence of HCDR1 is SEQ ID NO: 9, the amino acid sequence of HCDR2 is SEQ ID NO: 10, and the amino acid sequence of HCDR3 is SEQ ID NO: 11. In a more particular embodiment, Xaa at position 6 of the amino acid sequence given by SEQ ID NO: 11 is Ala; Xaa at position 14 of the amino acid sequence given by SEQ ID NO: 11 is Pro; and Xaa at position 4 of the amino acid sequence given by SEQ ID NO: 14 is Trp. In another more particular embodiment, Xaa at position 6 of the amino acid sequence given by SEQ ID NO: 11 is Arg; Xaa at position 14 of the amino acid sequence given by SEQ ID NO: 11 is Tyr; and Xaa at position 4 of the amino acid sequence given by SEQ ID NO: 14 is Asn.

As used herein, an "antibody" can be a human, humanized, murine, or mouse-rat chimera. An antibody is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. The functional ability of an antibody to bind a particular antigen is largely influenced by the six CDRs. Assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), and North numbering convention (North et al., A New Clustering of Antibody CDR Loop Conformations, Journal of Molecular Biology, 406:228-256 (2011)). The CDRs of the antibodies of the present invention are defined according to Table 1.

TABLE 1

CDR numbering conventions used to define the CDRs of the antibodies of the present invention.

| CDR | Starting Amino Acid Residue Defined By: | Ending Amino Acid Residue Defined By: |
| --- | --- | --- |
| HCDR1 | North | Kabat |
| HCDR2 | Kabat | Kabat |
| HCDR3 | North | Kabat |
| LCDR1 | Kabat | Kabat |
| LCDR2 | North | Kabat |
| LCDR3 | Kabat | Kabat |

The antibodies of the present invention are monoclonal antibodies ("mAbs"). The mAbs for the present invention are complete mAbs containing 2 HCs and 2 LCs. As referred to herein, mAbs are antibodies derived from a single copy or clone including, for example, any eukaryotic, prokaryotic or phage clone, and not the method by which it is produced. Monoclonal antibodies can be produced, for example, by hybridoma technologies, recombinant technologies, phage display technologies, synthetic technologies, e.g., CDR-grafting, or combinations of such or other technologies known in the art. Methods of producing and purifying antibodies are well known in the art and can be found, for example, in Harlow and Lane (1988), Antibodies, A Laboratory Manual, Cold Spring Harbor Laboratory Press, Cold Spring harbor, N.Y., chapters 5-8 and 15, ISBN 0-87969-314-2.

The monoclonal antibodies of the present invention may be prepared and purified using known methods. For example, cDNA sequences encoding a HC (for example the amino acid sequence given by SEQ ID NO: 1) and a LC (for example, the amino acid sequence given by SEQ ID NO: 2) may be cloned and engineered into a GS (glutamine synthetase) expression vector. The engineered immunoglobulin expression vector may then be stably transfected into CHO cells. As one of skill in the art will appreciate, mammalian expression of antibodies will result in glycosylation, typically at highly conserved N-glycosylation sites in the Fc region. Stable clones may be verified for expression of an antibody specifically binding to RANKL. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The monoclonal antibodies of the present invention can be used in the treatment of patients. More particularly the antibodies of the present invention are expected to treat bone-related disorders such as osteoporosis, osteopenia, and arthritis (such as rheumatoid arthritis), and skeletal abnormalities caused by cancers such as non-small cell lung cancer and multiple myeloma. As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from a reduction in RANKL activity, and includes: (a) inhibiting further progression of the disease; and (b) relieving the disease, i.e., causing regression of the disease or disorder or alleviating symptoms or complications thereof.

As used interchangeably herein, the term "patient" refers to a human. In certain embodiments, the patient is further characterized with a disease, disorder, or condition (e.g., a bone-related disorder) that would benefit from a reduction in RANKL activity.

As used herein, the term "bind" (or "binds") RANKL refers to an interaction of an antibody with an epitope of human RANKL. Preferably, "binds" refers to an interaction of an antibody of the present invention with an epitope as determined by hydrogen deuterium exchange (for example, see Example 4). Preferably, the epitope is a conformational epitope of human RANKL. In an embodiment, the term "bind" (or "binds") RANKL refers to an interaction with a conformational epitope of human RANKL, wherein the epitope is one or more of residues 89-97, and one or more of residues 125-132, of SEQ ID NO: 17. In another embodiment, the epitope is at least two amino acids of residues 89-97, and at least two amino acids of residues 125-132, of SEQ ID NO: 17. In another embodiment, the epitope is at least three amino acids of residues 89-97, and at least three amino acids of residues 125-132, of SEQ ID NO: 17. In another embodiment, the epitope is at least four amino acids of residues 89-97, and at least four amino acids within 125-132, of SEQ ID NO: 17. In another embodiment, the conformational epitope is at least five amino acids of residues 89-97, and at least five amino acids of residues 125-132, of SEQ ID NO: 17.

The term "epitope" as used herein refers to discrete, three-dimensional sites of an antigen that are recognized by the monoclonal antibodies of the present invention. The epitope may be determined by methods currently known in the art such as hydrogen deuterium exchange, alanine scanning, or X-ray crystallography. As used herein, "competing"

or "competition" refers to an antibody that is capable of inhibiting or blocking any one of the antibodies of the present invention from binding to human RANKL. An antibody is capable of inhibiting or blocking binding if, for example, there is a reduction or complete loss of binding by any one of the antibodies of the present invention to human RANKL in the presence of another antibody.

A monoclonal antibody of the present invention can be incorporated into a pharmaceutical composition which can be prepared by methods well known in the art and comprise a monoclonal antibody of the present invention and one or more pharmaceutically acceptable carrier(s) and/or diluent(s).

A pharmaceutical composition comprising a monoclonal antibody of the present invention can be administered to a patient at risk for, or exhibiting, diseases or disorders as described herein by parental routes (e.g., subcutaneous, intravenous, intraperitoneal, intramuscular, or transdermal). A pharmaceutical composition of the present invention contains an "effective" or "therapeutically effective" amount, as used interchangeably herein, of a monoclonal antibody of the present invention. An effective amount refers to an amount necessary (at dosages and for periods of time and for the means of administration) to achieve the desired therapeutic result. An effective amount of the monoclonal antibody may vary according to factors such as the disease state, age, sex, and weight of the individual, and the ability of the monoclonal antibody to elicit a desired response in the individual. An effective amount is also one in which any toxic or detrimental effects of the monoclonal antibody of the present invention are outweighed by the therapeutically beneficial effects.

EXAMPLES

Example 1: Antibody Expression and Purification

An exemplified antibody of the present invention is expressed and purified essentially as follows. A glutamine synthetase (GS) expression vector containing the polynucleotide sequences given by SEQ ID NO: 15 (encoding an exemplified heavy chain of SEQ ID NO: 1) and SEQ ID NO: 16 (encoding an exemplified light chain of SEQ ID NO: 2) is used to transfect a Chinese hamster cell line (CHO, GS knockout), by electroporation. The expression vector encodes a SV Early (Simian Virus 40E) promoter and the gene for GS. Expression of GS allows for the biochemical synthesis of glutamine, an amino acid required by the CHO cells. Posttransfection, cells undergo bulk selection with 50 uM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells. Transfected pools are plated at low density to allow for close-to-clonal outgrowth of stable expressing cells. The master-wells are screened for antibody expression and then scaled up in serum-free, suspension cultures to be used for production.

Clarified medium, into which the exemplified antibody has been secreted, is applied to a Protein A affinity column that has been equilibrated with a compatible buffer such as phosphate buffered saline (pH 7.4). The column is washed to remove nonspecific binding components. The bound antibody is eluted, for example, by pH gradient and neutralized for example with Tris, pH 8 buffer. Antibody fractions are detected, such as by SDS-PAGE or analytical size-exclusion, and then are pooled. Soluble aggregate and multimers may be effectively removed by common techniques including size exclusion, hydrophobic interaction, Capto multimodal chromatography, ion exchange, or hydroxyapatite chromatography. The antibody is concentrated and/or sterile filtered using common techniques. The purity of the exemplified antibody after these chromatography steps is greater than 98% (monomer). The antibody may be immediately frozen at −70° C. or stored at 4° C. for several months.

Example 2: Binding Affinity

The BIAcore® 2000 instrument is used to measure binding affinity. All measurements are performed at 25° C. 2 ug/mL of exemplified antibody of Example 1 is dissolved in HBS-EP buffer (150 mM sodium chloride, 3 mM EDTA, 0.005% (w/v) surfactant P-20, and 10 mM HEPES, pH7.4). Protein A is immobilized on flow cells 1 to 4 of a CM4 sensor chip at a level of 500 response units (Rus) using an amine coupling kit.

Binding is evaluated using multiple analytical cycles. Each cycle is performed at a flow rate of 20 uL/minute. About 10 uL of the exemplified antibody of Example 1, at a concentration of 2 ug/mL, is injected, aiming to capture about 100-200Rus; 250 uL of human RANKL (starting at 5 nM and using two-fold serial dilutions for each cycle) is injected, ten minutes is given for dissociation, and 10 uL of 10 mM glycine hydrochloride, pH 1.5 is used for regeneration. Association and dissociation rates for each cycle are evaluated using a "1:1 with mass transfer" binding model in the BIAevaluation software.

During engineering of the exemplified antibody of Example 1, presence of a leucine at the third from last position of HCDR3 (e.g., residue 12 of HCDR3 given by SEQ ID NO: 11) was identified as essential for conferring the engineered improved affinity to human RANKL of antibodies of the present invention. For example, in directed mutation analysis, if leucine was not present at the third from last position of HCDR3 (e.g., isoleucine was substituted for leucine), additional amino acid changes to antibodies of the present invention were not able to increase affinity to RANKL.

According to procedures essentially as described above, the antibody binds human RANKL with a $K_D$ of 2.82 pM, rat RANKL with a $K_D$ of 34.43 pM, and mouse RANKL with a $K_D$ of 6.64 pM. These data demonstrate that the exemplified antibody of Example 1 has high affinity binding to human and murine RANKL, with $K_D$ less than 10 pM.

Example 3: Neutralization of RANKL-Induced NF-kB-Driven Luciferase Activity in Vitro HEK293 cells, which stably co-express human RANK and a NF-kB driven luciferase reporter, are used to assess the ability of the exemplified antibody of Example 1 to neutralize RANKL activity. In this HEK293 cell model, RANK, when bound by human RANKL, induces NF-kB signaling which results in luciferase luminescence. Neutralization of RANKL binding to RANK, by the exemplified antibody of Example 1, is measured by a reduction of luciferase luminescence.

HEK293 cells are routinely cultured under selective pressure of 700 ug/mL Geneticin. 25,000 cells/well are added to the wells of 96 well tissue culture plates in assay media (50 uL DMEM/F12 (1:3) media containing 0.5% FBS, 20 nM Hepes, 1×GlutaMax, and 1× penicillin/streptomycin. Cells are incubated at 37° C. (with 5% CO2 and 95% humidity) overnight.

Assay media including 1 nM and 10 nM concentrations of human RANKL are used to prepare dose ranges of 10 nM to 0.005 nM (with 1:3 serial dilutions) for the exemplified antibody of Example 1, and doses are incubated for 15 minutes at room temperature. Assay medium is used for a "media only" control. Thereafter, 50 ul of antibody is added to 50 ul of media containing cultured cells and are incubated overnight at 37° C.

Following overnight incubation, existing growth media is removed and cells are suspended in 50 uL of BugLite (2.296 g DTT (Sigma), 1.152 g Coenzyme A, and 0.248 g ATP) in 1 L 1% Triton X-100 Lysis Buffer (30 mL Triton X-100, 3 mL MgCl, 108.15 mL 1M Trizma HCL, 41.85 mL 1M Trizma Base, and 817 mL H2O). Cells are then lysed with gentle agitation on a plate shaker for between 5 to 10 minutes. Following cell lysis, luminescence is measured on a plate reader (Envision Plate Reader). $IC_{50}$ values for all treatment groups are calculated using a three-parameter logistic regression model with GraphPad Prism 6.

Following a procedure essentially as described above, the $IC_{50}$ for the antibody binding to human RANKL was 0.069 nM. The results demonstrate that the exemplified antibody of Example 1 antibody neutralizes human RANKL induced NF-kB driven luciferase luminescence. Media controls did not neutralize human RANKL induced NF-kB driven luciferase luminescence in the HEK293 cell model at any concentration tested.

Example 4: Epitope Mapping by Hydrogen Deuterium Exchange

Hydrogen deuterium exchange with mass spectrometry (HDXMS) is performed in order to determine where the exemplified antibody of Example 1 binds the RANKL protein. This method has been used successfully to map epitopes of several antibodies (Obungu et. al. 2009 *Biochemistry*, 48:7251-60 Lu et. al. 2005 *Biochemistry* 44:11106-14).

A RANKL/antibody complex was made by mixing 10 μs of a human RANKL solution with 10 μg of exemplified antibody of Example 1, and then diluting with 1×PBS. The complexes for protein surface labeling study are labeled with acetic acid hydroxylsuccinimide ester, and HDXMS analysis is performed by mixing 4 μL of RANKL/antibody complex with 16 μL of 100% $D_2O$ (80% D during exchange) and the mixture held at ambient temperature for 60 seconds. The exchange is quenched with 50 μL of 0.1 N HCl at 0° C., immediately treated with 2 μL of 2 mg/mL pepsin solution at 0° C. for 3.5 minutes, and then manually injected on RP-HPLC column. LC/MS/MS analysis is thereafter done on the digest solutions by a Waters SYNAPT mass spectrometry coupled with a Waters Acquity UPLC.

Following procedures essentially as described above, two human RANKL peptides, 239-272 and 281-290, showed significant negative delta. This analysis demonstrated that RANKL epitope for the exemplified antibody of Example 1 is conformational and is amino acids 89-97 and 125-132 of SEQ ID NO: 17. The first region (89-97) is identical for human and rodent RANKL. The other region (125-132) is identical in both human and rodent RANKL except a single amino acid difference in position 129 where the serine is replaced with an alanine in rodent RANKL.

Example 5: Effects on Bone Mass Density, In Vivo, are Assessed Using an Intact Female Murine Model C57/B6 intact female mice, aged twenty to twenty-two weeks (Charles River) are maintained on a 12 hour light/dark cycle at 22° C. with ad lib access to food (TD 2014 with 0.72% Ca and 0.61% P, Vit. D 0.99 IU/g, Teklad, Madison, Wis.) and water.

The mice are divided into animals treated with a weekly subcutaneous injection of 10 mg/kg of the exemplified antibody of Example 1 (n=6 animals) or a PBS vehicle control. Mice are sacrificed at four weeks. Bone mass density (BMD) of distal and mid-femur is monitored by quantitative computed tomography (qCT) using Aloka LaTheta LTC-100 model CT scanner.

Following a procedure essentially as described above, animals treated with the antibody had a 23% increase in distal femur BMD, and a 4% increase in middle femur BMD compared to control animals. These results demonstrate that animals dosed weekly with the exemplified antibody of Example 1 have increased BMD at both the distal and middle femur.

Example 6: In Vivo Efficacy Analysis in Ovariectomized Murine Model

In vivo effects on bone mass density are assessed using an ovariectomized murine model. Twenty week old female C57/B6 mice (Harlan, Indianapolis, Ind.) are ovariectomized (or sham operated control group) and maintained on a 12 hour light/dark cycle at 22° C. with ad lib access to food (TD 2014 with 0.72% Ca and 0.61% P, Vit. D 0.99 IU/g, Teklad, Madison, Wis.) and water. Osteopenia is established in the mice by allowing ovariectomized mice to lose bone mass for a six-week period.

Following a six-week osteopenia-establishing period, mice are divided into treatment groups (n=6 animals each group) or a vehicle PBS control group. Each treatment group of mice receives a weekly subcutaneous injection of 3 mg/kg or 10 mg/kg of the exemplified antibody of Example 1, or PBS. Mice are sacrificed at four weeks. Skeletal bone mass density (BMD) of vertebrae 5 is assessed by quantitative computed tomography (qCT), using Aloka LaTheta LTC-100 model CT scanner, following sacrifice.

Following a procedure essentially as described above, animals treated with 3 mg/kg antibody had a 2% increase in BMD, and animals treated with 10 mg/kg antibody had an 11% increase in BMD compared to controls. These results demonstrate that, dosed weekly, the exemplified antibody of Example 1 results in a dose-dependent increase of BMD of vertebrae in ovariectomized mice.

Example 7: In Vivo Efficacy Analysis in Orchidectomized Murine Model

In vivo effects on bone mass density and bone mineral content are assessed using an orchidectomized murine model. Sixteen week old male C57/B6 mice (Harlan, Indianapolis, Ind.) are orchidectomized (or vehicle control group, n=6) and maintained on a 12 hour light/dark cycle at 22° C. with ad lib access to food (TD 2014 with 0.72% Ca and 0.61% P, Vit. D 0.99 IU/g, Teklad, Madison, Wis.) and water. Osteopenia is established in the orchidectomized mice by allowing mice to lose bone mass for a six-week period.

Following a six-week osteopenia-establishing period, 9 mice receive subcutaneous injections of a 2 mg/kg dose of the exemplified antibody of Example 1 twice per week. Animals injected with PBS serve as controls. Mice are sacrificed at two weeks. Bone mass density (BMD) of distal femur and bone mineral content (BMC) of lumbar vertebra are assessed by quantitative computed tomography (qCT) using Aloka LaTheta LTC-100 model CT scanner.

Following a procedure essentially as described above, mice treated with the antibody had a 19% increase in distal femur BMD, and a 13% increase in lumbar vertebra, compared to control animals. These results demonstrate that treatment with the exemplified antibody of Example 1 results in an increase of BMD of distal femur and of lumbar vertebra in orchidectomized mice.

Sequences

Exemplified HC (SEQ ID NO: 1)
QVQLVQSGAEVKKPGSSVKVSCKASGYAFTNYYIEWVRQAPGQGLEWMGVINPGWGDTNYNEKFKGRVTITADKSTSTA
YMELSSLRSEDTAVYYCARRDTAHGYYALDPWGQGTTVTVSSASTKGPSVFPLAPCSRSTSESTAALGCLVKDYFPEPV
TVSWNSGALTSGVHTFPAVLQSSGLYSLSSVVTVPSSSLGTKTYTCNVDHKPSNTKVDKRVESKYGPPCPPCPAPEAAG
GPSVFLFPPKPKDTLMISRTPEVTCVVVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVKGFYPSDIAVEWESNGQPENNYKTT
PPVLDSDGSFFLYSRLTVDKSRWQEGNVFSCSVMHEALHNHYTQKSLSLSLG Exemplified LC (SEQ ID NO: 2)
DIQMTQSPSSLSASVGDRVTITCKASQNVGTNVAWYQQKPGKAPKLLIYSASYRYSGVPSRFSGSGSGTDFTLTISSLQ
PEDFATYYCQQYWDYPLTFGGGTKVEIKRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC Exemplified HCVR (SEQ ID NO: 3)
QVQLVQSGAEVKKPGSSVKVSCKASGYAFTNYYIEWVRQAPGQGLEWMGVINPGWGDTNYNEKFKGRVTITADKSTSTA
YMELSSLRSEDTAVYYCARRDTAHGYYALDPWGQGTTVTVSS Exemplified LCVR (SEQ ID NO: 4)
DIQMTQSPSSLSASVGDRVTITCKASQNVGTNVAWYQQKPGKAPKLLIYSASYRYSGVPSRFSGSGSGTDFTLTISSLQ
PEDFATYYCQQYWDYPLTFGGGTKVEIK Exemplified HC (SEQ ID NO: 5)
QVQLQQSGAELVRPGTSVKVSCKASGYAFTNYYIEWLKQRPGQGLEWIGVINPGWGDTNYNEKFKGKATLTADKSSSTA
YMQLSSLTSDDSAVFFCARRDTRHGYYALDYWGQGTSVTVSSAKTTPPSVYPLAPGTALKSNSMVTLGCLVKGYFPEPV
TVTWNSGALSSGVHTFPAVLQSGLYTLTSSVTVPSSTWPSQTVTCNVAHPASSTKVDKKIVPRNCGGDCKPCICTGSEV
SSVFIFPPKPKDVLTITLTPKVTCVVVDISQDDPEVHFSWFVDDVEVHTAQTRPPEEQFNSTFRSVSELPILHQDWLNG
RTFRCKVTSAAFPSPIEKTISKPEGRTQVPHVYTMSPTKEEMTQNEVSITCMVKGFYPPDIYVEWQMNGQPQENYKNTP
PTMDTDGSYFLYSKLNVKKEKWQQGNTFTCSVLHEGLHNHHTEKSLSHSPG Exemplified LC (SEQ ID NO: 6)
DIVMTQSQKFMSTSVGDRVSVTCKASQNVGTNVAWYQQKPGQSPKALIYSASYRYSGVPDRFTGSGSGTDFTLTISNVQ
SEDLAEYFCQQYNDYPLTFGAGTRLEIKRADAAPTVSIFPPSTEQLATGGASVVCLMNNFYPRDISVKWKIDGTERRDG
VLDSVTDQDSKDSTYSMSSTLSLSKADYESHNLYTCEVVHKTSSSPVVKSFNRNEC Exemplified HCVR (SEQ ID NO: 7)
QVQLQQ SGAELVRPGTSVKVSCKASGYAFTNYYIEWLKQRPGQGLEWIGVINPGWGDTNYNEKFKGKATLTADKSSST
AYMQLSSLTSDDSAVFFCARRDTRHGYYALDYWGQGTSVTVSS Exemplified LCVR (SEQ ID NO: 8)
DIVMTQSQKFMSTSVGDRVSVTCKASQNVGTNVAWYQQKPGQSPKALIYSASYRYSGVPDRFTGSGSGTDFTLTISNVQ
SEDLAEYFCQQYNDYPLTFGAGTRLEIK Exemplified HCDR1 (SEQ ID NO: 9)
KASGYAFTNYYIE Exemplified HCDR2 (SEQ ID NO: 10)
VINPGWGDTNYNEKFKG Exemplified HCDR3 (SEQ ID NO: 11)
ARRDTXHGYYALDX
Wherein X at position 6 is Ala or Arg, and X at position 14 is Pro or Tyr.

Exemplified LCDR1 (SEQ ID NO: 12)
KASQNVGTNVA

Exemplified LCDR2 (SEQ ID NO: 13)
YSASYRYS

Exemplified LCDR3 (SEQ ID NO: 14)
QQYXDYPLT
Wherein X at position 4 is Trp or Asn.

Exemplified DNA encoding the HC protein of SEQ ID NO: 1 (SEQ ID NO: 15)
CAGGTGCAGCTGGTGCAGTCTGGGGCTGAGGTGAAGAAGCCTGGGTCCTCAGTGAAGGTTTCCTGCAAGGCATCGGCT
ACGCCTTCACCAACTACTATATCGAGTGGGTGCGACAGGCCCCTGGACAAGGGCTTGAGTGGATGGGAGTGATCAACCC
CGGCTGGGGCGACACGAACTACAACGAGAAGTTCAAGGGCAGAGTCACCATTACCGCGGACAAATCCACGAGCACAGCC
TACATGGAGCTGAGCAGCCTGAGATCTGAGGACACGGCCGTGTATTACTGTGCGAGACGCGATACGGCTCACGGCTACT
ACGCCCTTGATCCGTGGGGCCAAGGAACCACGGTCACCGTCTCCTCAGCCTCCACCAAGGGCCCATCGGTCTTCCCGCT
AGCGCCCTGCTCCAGGAGCACCTCCGAGAGCACAGCCGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTCCTCAGGACTCTACT
CCCTCAGCAGCGTGGTGACCGTGCCCTCCAGCAGCTTGGGCACCAAGACCTACACCTGCAACGTAGATCACAAGCCCAG
CAACACCAAGGTGGACAAGAGAGTTGAGTCCAAATATGGTCCCCCATGCCCACCCTGCCCAGCACCTGAGGCCGCCGGG
GGACCATCAGTCTTCCTGTTCCCCCCAAAACCCAAGGACACTCTCATGATCTCCCGGACCCCTGAGGTCACGTGCGTGG
TGGTGGACGTGAGCCAGGAAGACCCCGAGGTCCAGTTCAACTGGTACGTGGATGGCGTGGAGGTGCATAATGCCAAGAC
AAAGCCGCGGGAGGAGCAGTTCAACAGCACGTACCGTGTGGTCAGCGTCCTCACCGTCCTGCACCAGGACTGGCTGAAC
GGCAAGGAGTACAAGTGCAAGGTCTCCAACAAAGGCCTCCCGTCCTCCATCGAGAAAACCATCTCCAAAGCCAAAGGGC

```
AGCCCCGAGAGCCACAGGTGTACACCCTGCCCCCATCCCAGGAGGAGATGACCAAGAACCAGGTCAGCCTGACCTGCCT
GGTCAAAGGCTTCTACCCCAGCGACATCGCCGTGGAGTGGGAAAGCAATGGGCAGCCGGAGAACAACTACAAGACCACG
CCTCCCGTGCTGGACTCCGACGGCTCCTTCTTCCTCTACAGCAGGCTAACCGTGGACAAGAGCAGGTGGCAGGAGGGGA
ATGTCTTCTCATGCTCCGTGATGCATGAGGCTCTGCACAACCACTACACACAGAAGAGCCTCTCCCTGTCTCTGGGT
```

Exemplified DNA encoding the LC of SEQ ID NO: 2 (SEQ ID NO: 16)
```
GACATCCAGATGACCCAGTCTCCATCCTCTCTGTCTGCATCTGTAGGAGACAGAGTCACCATCACTTGCAAGGCCAGCC
AGAATGTGGGCACCAACGTGGCCTGGTATCAGCAGAAACAGGGAAAGCCCCTAAGCTCCTGATCTATAGCGCCAGCTA
CAGATACAGCGGGGTCCCATCAAGGTTCAGTGGCAGTGGATCTGGGACAGATTTCACTCTCACCATCAGCAGTCTGCAA
CCTGAAGATTTTGCAACTTACTACTGTCAGCAGTACTGGGACTACCCCCTGACCTTCGGCGGAGGGACCAAGGTGGAGA
TCAAACGGACTGTGGCTGCACCATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGGATAACGCCCTCCAATGGGTAAC
TCCCAGGAGAGTGTCACAGAGCAGGACAGCAAGGACAGCACCTACAGCCTCAGCAGCACCCTGACGCTGAGCAAAGCAG
ACTACGAGAAACACAAAGTCTACGCCTGCGAAGTCACCCATCAGGGCCTGAGCTCGCCCGTCACAAAGAGCTTCAACAG
GGGAGAGTGC
```

RANKL Extracellular Domain (SEQ ID NO: 17)
```
MSKLEAQPFAHLTINATDIPSGSHKVSLSSWYHDRGWAKISNMTFSNGKLIVNQDGFYYLYANICFRHHETSGDLATEY
LQLMVYVTKTSIKIPSSHTLMKGGSTKYWSGNSEFHFYSINVGGFFKLRSGEEISIEVSNPSLLDPDQDATYFGAFKVR
DID
```

We claim:

1. An antibody that binds human RANKL, comprising a light chain variable region (LCVR) and a heavy chain variable region (HCVR), wherein the LCVR comprises complementarity determining regions (CDRs) LCDR1, LCDR2, and LCDR3, and the HCVR comprises CDRs HCDR1, HCDR2, and HCDR3, wherein the amino acid sequence of LCDR1 is SEQ ID NO: 12, the amino acid sequence of LCDR2 is SEQ ID NO: 13, the amino acid sequence of LCDR3 is SEQ ID NO: 14, the amino acid sequence of HCDR1 is SEQ ID NO: 9, the amino acid sequence of HCDR2 is SEQ ID NO: 10, and the amino acid sequence of HCDR3 is SEQ ID NO: 11.

2. The antibody of claim 1, wherein:
 a. Xaa at position 6 of the amino acid sequence given by SEQ ID NO: 11 is Ala;
 b. Xaa at position 14 of the amino acid sequence given by SEQ ID NO: 11 is Pro; and
 c. Xaa at position 4 of the amino acid sequence given by SEQ ID NO: 14 is Trp.

3. The antibody of claim 1, wherein:
 a. Xaa at position 6 of the amino acid sequence given by SEQ ID NO: 11 is Arg;
 b. Xaa at position 14 of the amino acid sequence given by SEQ ID NO: 11 is Tyr; and
 c. Xaa at position 4 of the amino acid sequence given by SEQ ID NO: 14 is Asn.

4. The antibody of claim 1, comprising a light chain variable region (LCVR) and a heavy chain variable region (HCVR), wherein the amino acid sequence of the LCVR is SEQ ID NO: 4 or SEQ ID NO: 8, and the amino acid sequence of the HCVR is SEQ ID NO: 3 or SEQ ID NO: 7.

5. The antibody of claim 4, wherein the amino acid sequence of the LCVR is SEQ ID NO: 4, and the amino acid sequence of the HCVR is SEQ ID NO: 3.

6. The antibody of claim 4, wherein the amino acid sequence of the LCVR is SEQ ID NO: 8, and the amino acid sequence of the HCVR is SEQ ID NO: 7.

7. The antibody of claim 1, comprising a light chain (LC) and a heavy chain (HC), wherein the amino acid sequence of the LC is SEQ ID NO: 2 or SEQ ID NO: 6, and the amino acid sequence of the HC is SEQ ID NO: 1 or SEQ ID NO: 5.

8. The antibody of claim 7, wherein the amino acid sequence of the LC is SEQ ID NO: 2, and the amino acid sequence of the HC is SEQ ID NO: 1.

9. The antibody of claim 7, wherein the amino acid sequence of the LC is SEQ ID NO: 6, and the amino acid sequence of the HC is SEQ ID NO: 5.

10. A pharmaceutical composition comprising the antibody of claim 1, and one or more pharmaceutically acceptable carriers, diluents, or excipients.

* * * * *

SEQUENCE LISTING

<160> NUMBER OF SEQ ID NOS: 17

<210> SEQ ID NO 1
<211> LENGTH: 447
<212> TYPE: PRT
<213> ORGANISM: Artificial Sequence
<220> FEATURE:
<223> OTHER INFORMATION: Exemplified HC

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Tyr Ile Glu Trp Val Arg Gln Ala Pro Gly Gln Gly Leu Glu Trp Met
        35                  40                  45

Gly Val Ile Asn Pro Gly Trp Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Thr Ala His Gly Tyr Tyr Ala Leu Asp Pro Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205
```

```
Lys Pro Ser Asn Thr Lys Val Asp Lys Arg Val Glu Ser Lys Tyr Gly
            210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
                435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Exemplified LC

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 121
<212> TYPE: PRT
<213> ORGANISM: Artificial Sequence
<220> FEATURE:
<223> OTHER INFORMATION: Exemplified HCVR

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Asn Tyr
            20                  25                  30

Tyr Ile Glu Trp Val Arg Gln Ala Pro Gly Gln Gly Leu Glu Trp Met
        35                  40                  45

Gly Val Ile Asn Pro Gly Trp Gly Asp Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Thr Ala His Gly Tyr Tyr Ala Leu Asp Pro Trp Gly
            100                 105                 110

Gln Gly Thr Thr Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Exemplified LCVR

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Trp Asp Tyr Pro Leu
                85                  90                  95

Thr Phe Gly Gly Gly Thr Lys Val Glu Ile Lys
            100                 105

<210> SEQ ID NO 5
<211> LENGTH: 446
<212> TYPE: PRT
<213> ORGANISM: Artificial Sequence
<220> FEATURE:
<223> OTHER INFORMATION: Exemplified HC

<400> SEQUENCE: 5

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
                20                  25                  30

Tyr Ile Glu Trp Leu Lys Gln Arg Pro Gly Gln Gly Leu Glu Trp Ile
            35                  40                  45

Gly Val Ile Asn Pro Gly Trp Gly Asp Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Phe Phe Cys
                85                  90                  95

Ala Arg Arg Asp Thr Arg His Gly Tyr Tyr Ala Leu Asp Tyr Trp Gly
                100                 105                 110

Gln Gly Thr Ser Val Thr Val Ser Ser Ala Lys Thr Thr Pro Pro Ser
            115                 120                 125

Val Tyr Pro Leu Ala Pro Gly Thr Ala Leu Lys Ser Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ala Leu Ser Ser Gly Val His Thr Phe Pro Ala
                165                 170                 175

Val Leu Gln Ser Gly Leu Tyr Thr Leu Thr Ser Ser Val Thr Val Pro
            180                 185                 190

Ser Ser Thr Trp Pro Ser Gln Thr Val Thr Cys Asn Val Ala His Pro
    195                 200                 205

Ala Ser Ser Thr Lys Val Asp Lys Lys Ile Val Pro Arg Asn Cys Gly
210                 215                 220

Gly Asp Cys Lys Pro Cys Ile Cys Thr Gly Ser Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Asp Ile Ser Gln Asp Asp Pro Glu
            260                 265                 270

Val His Phe Ser Trp Phe Val Asp Asp Val Glu Val His Thr Ala Gln
    275                 280                 285

Thr Arg Pro Pro Glu Glu Gln Phe Asn Ser Thr Phe Arg Ser Val Ser
290                 295                 300

Glu Leu Pro Ile Leu His Gln Asp Trp Leu Asn Gly Arg Thr Phe Arg
305                 310                 315                 320

Cys Lys Val Thr Ser Ala Ala Phe Pro Ser Pro Ile Glu Lys Thr Ile
                325                 330                 335

Ser Lys Pro Glu Gly Arg Thr Gln Val Pro His Val Tyr Thr Met Ser
                340                 345                 350

Pro Thr Lys Glu Glu Met Thr Gln Asn Glu Val Ser Ile Thr Cys Met
            355                 360                 365

Val Lys Gly Phe Tyr Pro Pro Asp Ile Tyr Val Glu Trp Gln Met Asn
        370                 375                 380

Gly Gln Pro Gln Glu Asn Tyr Lys Asn Thr Pro Pro Thr Met Asp Thr
385                 390                 395                 400

Asp Gly Ser Tyr Phe Leu Tyr Ser Lys Leu Asn Val Lys Lys Glu Lys
                405                 410                 415

Trp Gln Gln Gly Asn Thr Phe Thr Cys Ser Val Leu His Glu Gly Leu
            420                 425                 430

His Asn His His Thr Glu Lys Ser Leu Ser His Ser Pro Gly
        435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Exemplified LC

<400> SEQUENCE: 6

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asp Tyr Pro Leu
                85                  90                  95

Thr Phe Gly Ala Gly Thr Arg Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Ser Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210

<210> SEQ ID NO 7
<211> LENGTH: 121
<212> TYPE: PRT
<213> ORGANISM: Artificial Sequence
<220> FEATURE:
<223> OTHER INFORMATION: Exemplified HCVR

<400> SEQUENCE: 7

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Tyr Ile Glu Trp Leu Lys Gln Arg Pro Gly Gln Gly Leu Glu Trp Ile
        35                  40                  45

Gly Val Ile Asn Pro Gly Trp Gly Asp Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Phe Phe Cys
                85                  90                  95

Ala Arg Arg Asp Thr Arg His Gly Tyr Tyr Ala Leu Asp Tyr Trp Gly
            100                 105                 110

Gln Gly Thr Ser Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Exemplified LCVR

<400> SEQUENCE: 8

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asp Tyr Pro Leu
                85                  90                  95

Thr Phe Gly Ala Gly Thr Arg Leu Glu Ile Lys
            100                 105

<210> SEQ ID NO 9
<211> LENGTH: 13
<212> TYPE: PRT
<213> ORGANISM: Artificial Sequence
<220> FEATURE:
<223> OTHER INFORMATION: Exemplified HCDR1

<400> SEQUENCE: 9

Lys Ala Ser Gly Tyr Ala Phe Thr Asn Tyr Tyr Ile Glu
1               5                   10

<210> SEQ ID NO 10
<211> LENGTH: 17
<212> TYPE: PRT
<213> ORGANISM: Artificial Sequence

```
<220> FEATURE:
<223> OTHER INFORMATION: Exemplified HCDR2

<400> SEQUENCE: 10

Val Ile Asn Pro Gly Trp Gly Asp Thr Asn Tyr Asn Glu Lys Phe Lys
1               5                   10                  15

Gly

<210> SEQ ID NO 11
<211> LENGTH: 14
<212> TYPE: PRT
<213> ORGANISM: Artificial Sequence
<220> FEATURE:
<223> OTHER INFORMATION: Exemplified HCDR3
<220> FEATURE:
<221> NAME/KEY: MISC_FEATURE
<222> LOCATION: (6)..(6)
<223> OTHER INFORMATION: Xaa at pos. 6 is Ala or Arg
<220> FEATURE:
<221> NAME/KEY: MISC_FEATURE
<222> LOCATION: (14)..(14)
<223> OTHER INFORMATION: Xaa at pos. 14 is Pro or Tyr

<400> SEQUENCE: 11

Ala Arg Arg Asp Thr Xaa His Gly Tyr Tyr Ala Leu Asp Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Exemplified LCDR1

<400> SEQUENCE: 12

Lys Ala Ser Gln Asn Val Gly Thr Asn Val Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Exemplified LCDR2

<400> SEQUENCE: 13

Tyr Ser Ala Ser Tyr Arg Tyr Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Exemplified LCDR3
<220> FEATURE:
<221> NAME/KEY: MISC_FEATURE
<222> LOCATION: (4)..(4)
<223> OTHER INFORMATION: Xaa at pos. 4 is Trp or Asn

<400> SEQUENCE: 14

Gln Gln Tyr Xaa Asp Tyr Pro Leu Thr
1               5

<210> SEQ ID NO 15
<211> LENGTH: 1341
<212> TYPE: DNA
<213> ORGANISM: Artificial Sequence
```

```
<220> FEATURE:
<223> OTHER INFORMATION: Exemplified DNA encoding the HC of SEQ ID NO: 1

<400> SEQUENCE: 15
caggtgcagc tggtgcagtc tggggctgag gtgaagaagc ctgggtcctc agtgaaggtt      60
tcctgcaagg catctggcta cgccttcacc aactactata tcgagtgggt gcgacaggcc     120
cctggacaag gcttgagtg gatgggagtg atcaaccccg ctggggcga cacgaactac       180 aacgagaagt tcaagggcag agtcaccatt accgcggaca atccacgag cacagcctac      240 atggagctga gcagcctgag atctgaggac acggccgtgt attactgtgc gagacgcgat    300
acggctcacg gctactacgc ccttgatccg tggggccaag gaaccacggt caccgtctcc    360
tcagcctcca ccaagggccc atcggtcttc ccgctagcgc cctgctccag gagcacctcc    420
gagagcacag ccgccctggg ctgcctggtc aaggactact ccccgaacc ggtgacggtg     480 tcgtggaact caggcgccct gaccagcggc gtgcacacct tcccggctgt cctacagtcc    540
tcaggactct actccctcag cagcgtggtg accgtgccct ccagcagctt gggcacgaag    600
acctacacct gcaacgtaga tcacaagccc agcaacacca aggtggacaa gagagttgag    660
tccaaatatg gtccccatg cccacccctgc ccagcacctg aggccgccgg gggaccatca    720
gtcttcctgt tccccccaaa acccaaggac actctcatga tctcccggac ccctgaggtc    780
acgtgcgtgg tggtggacgt gagccaggaa gaccccgagg tccagttcaa ctggtacgtg    840
gatggcgtgg aggtgcataa tgccaagaca agccgcggg aggagcagtt caacagcacg     900
taccgtgtgg tcagcgtcct caccgtcctg caccaggact ggctgaacgg caaggagtac    960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaaa gcaatgggca gccggagaac aactacaaga ccacgcctcc cgtgctggac    1200
tccgacggct ccttcttcct ctacagcagg ctaaccgtgg acaagagcag gtggcaggag    1260
gggaatgtct tctcatgctc cgtgatgcat gaggctctgc acaaccacta cacacagaag    1320
agcctctccc tgtctctggg t                                              1341

<210> SEQ ID NO 16
<211> LENGTH: 642
<212> TYPE: DNA
<213> ORGANISM: Artificial Sequence
<220> FEATURE:
<223> OTHER INFORMATION: Exemplified DNA encoding the LC of SEQ ID NO: 2

<400> SEQUENCE: 16
gacatccaga tgacccagtc tccatcctct ctgtctgcat ctgtaggaga cagagtcacc      60
atcacttgca aggccagcca gaatgtgggc accaacgtgg cctggtatca gcagaaacca    120
gggaaagccc ctaagctcct gatctatagc gccagctaca gatacagcgg ggtcccatca    180
aggttcagtg gcagtggatc tgggacagat ttcactctca ccatcagcag tctgcaacct    240
gaagattttg caacttacta ctgtcagcag tactgggact accccctgac cttcggcgga    300
gggaccaagg tggagatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
```

```
ctgagcaaag cagactacga gaaacacaaa gtctacgcct gcgaagtcac ccatcagggc      600
ctgagctcgc ccgtcacaaa gagcttcaac aggggagagt gc                        642

<210> SEQ ID NO 17
<211> LENGTH: 161
<212> TYPE: PRT
<213> ORGANISM: Artificial Sequence
<220> FEATURE:
<223> OTHER INFORMATION: human RANKL

<400> SEQUENCE: 17

Met Ser Lys Leu Glu Ala Gln Pro Phe Ala His Leu Thr Ile Asn Ala
1               5                   10                  15

Thr Asp Ile Pro Ser Gly Ser His Lys Val Ser Leu Ser Ser Trp Tyr
            20                  25                  30

His Asp Arg Gly Trp Ala Lys Ile Ser Asn Met Thr Phe Ser Asn Gly
        35                  40                  45

Lys Leu Ile Val Asn Gln Asp Gly Phe Tyr Tyr Leu Tyr Ala Asn Ile
    50                  55                  60

Cys Phe Arg His His Glu Thr Ser Gly Asp Leu Ala Thr Glu Tyr Leu
65                  70                  75                  80

Gln Leu Met Val Tyr Val Thr Lys Thr Ser Ile Lys Ile Pro Ser Ser
                85                  90                  95

His Thr Leu Met Lys Gly Gly Ser Thr Lys Tyr Trp Ser Gly Asn Ser
            100                 105                 110

Glu Phe His Phe Tyr Ser Ile Asn Val Gly Gly Phe Phe Lys Leu Arg
        115                 120                 125

Ser Gly Glu Glu Ile Ser Ile Glu Val Ser Asn Pro Ser Leu Leu Asp
    130                 135                 140

Pro Asp Gln Asp Ala Thr Tyr Phe Gly Ala Phe Lys Val Arg Asp Ile
145                 150                 155                 160

Asp
```